United States Patent
Kim et al.

(10) Patent No.: US 7,246,532 B2
(45) Date of Patent: Jul. 24, 2007

(54) FLOW INDICATOR AND APPARATUS FOR MONITORING PARTICLES IN AIR

(75) Inventors: Dong-Hyun Kim, Yongin-si (KR); Bok-Seok Yang, Hwaseong-si (KR); Do-Hyun Cho, Yongin-si (KR); Hwan-Ki Choi, Hwaseong-si (KR); Jae-Han Koo, Yongin-si (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 0 days.

(21) Appl. No.: 11/431,521

(22) Filed: May 11, 2006

(65) Prior Publication Data
US 2006/0266133 A1  Nov. 30, 2006

(30) Foreign Application Priority Data
May 27, 2005  (KR) .................. 10-2005-0044890

(51) Int. Cl.
*G01N 1/00* (2006.01)
(52) U.S. Cl. .................................................. 73/865.5
(58) Field of Classification Search ............... 73/865.5
See application file for complete search history.

(56) References Cited

U.S. PATENT DOCUMENTS

| | | | |
|---|---|---|---|
| 3,699,560 A * | 10/1972 | Meunier et al. ............ 340/611 |
| 4,899,582 A * | 2/1990 | O'Dougherty ............... 73/168 |
| 4,928,514 A * | 5/1990 | Beaston ...................... 73/1.73 |
| 5,856,623 A | 1/1999 | Ahn et al. |
| 6,212,957 B1 * | 4/2001 | McCombs et al. ....... 73/861.55 |
| 6,594,001 B1 * | 7/2003 | Yabusaki ..................... 356/73 |
| 6,938,777 B2 * | 9/2005 | Call et al. ................... 209/143 |
| 2004/0139785 A1 * | 7/2004 | Abdul-Khalek ............ 73/28.01 |

FOREIGN PATENT DOCUMENTS

| | | |
|---|---|---|
| JP | 08-054265 | 2/1996 |
| KR | 1998-041514 | 8/1998 |
| KR | 10-0252215 | 1/2000 |

* cited by examiner

*Primary Examiner*—Robert Raevis
(74) *Attorney, Agent, or Firm*—Volentine & Whitt, PLLC

(57) ABSTRACT

A flow indicator comprising a housing and a floater and adapted to draw an air sample is provided. The housing has at least one lower inlet port, an interior space, an upper outlet port, and a transparent window. The floater is disposed inside the housing and is adapted to move substantially vertically in accordance with the flow of the air sample. The floater is also adapted to indicate a flow rate of the air sample.

4 Claims, 10 Drawing Sheets

FLOW INDICATOR AND APPARATUS FOR MONITORING PARTICLES IN AIR

BACKGROUND OF THE INVENTION

1. Field of the Invention

Embodiments of the invention relate to a flow indicator and an apparatus for monitoring particles in air. More particularly, embodiments of the invention relate to an apparatus adapted to draw an air sample from the air in a clean room and count particles contained in the air sample, and a flow indicator adapted to indicate the flow rate of the air sample.

This application claims priority to Korean Patent Application No. 10-2005-0044890, filed on May 27, 2005, the subject matter of which is hereby incorporated by reference in its entirety.

2. Description of the Related Art

Semiconductor devices are commonly manufactured by performing a complex sequence of fabrication processes that form a number of semiconductor dies, i.e., a number of electrical circuits individually formed on portions of a silicon wafer used as a substrate. Once the semiconductor dies have been formed on a silicon wafer an electrical die sorting (EDS) process is performed which inspects the electrical characteristics of the electrical circuits formed by the sequence of fabrication processes. Thereafter, individual semiconductor dies are removed from the silicon wafer and packaged to form a competed semiconductor device. This packaging process generally involves encapsulating each semiconductor die in an epoxy resin.

The sequence of fabrication processes usually includes one or more of: a deposition process adapted to deposit a material layer on the substrate; a chemical mechanical polishing (CMP) process adapted to planarize a material layer; a photolithography process adapted to form a photoresist pattern, an etching process adapted to form a pattern having desired electrical characteristics from a material layer using the photoresist pattern; an ion implantation process adapted to selectively implant ions into specific regions of the substrate; a cleaning process adapted to remove impurities from the substrate; a drying process adapted to dry cleaned substrate; an inspection process adapted to identify defects in the material layer and/or the pattern; etc.

Many if not all of these fabrication processes are performed in a conventional clean room. Clean rooms are widely used to prevent workpieces, such as silicon wafers, from becoming contaminated by particles in the air such as ordinary dust. The carefully controlled environment of a clean room is managed in accordance with various defined classes of cleanliness. Each clean room class is defined by the concentration of contaminant particles and/or the largest acceptable diameter of contaminate particles allowable within the clean room.

Various measurement apparatuses have been developed to facilitate clean room management. A condensation particle counter, which is one such measurement apparatus, operates under the principle that the particle size increases during an alcohol evaporation process. An optical particle counter, which is another conventional measurement apparatus, measures the intensity of light scattered from a projected laser by the particles in the sampled air.

Examples of particle monitoring apparatuses including such particle counters are disclosed, for example, in Japanese Patent Application Publication No. 8-054265, Korean Patent No. 252215, and U.S. Pat. No. 5,856,623.

One conventional particle monitoring apparatus includes a sampling probe adapted to draw in an air sample, and a particle counter connected to the sampling probe. The sampling probe is connected to the particle counter by a sampling tube, and the vacuum pressure (i.e., a suction force) used to draw in the air sample in provided by a pump disposed within the particle counter. In the conventional particle monitoring apparatus, the flow rate of the air sample varies in accordance with the suction force applied by the pump, the length of the sampling tube, leakage of the air sample throughout the apparatus, etc.

However, variations in the air sample flow rate cause problems in the management of clean room cleanliness. For example, when the air sample flow rate falls abnormally low, the exact of contaminate particles in the air cannot be accurately measured. Contamination of workpieces may result.

Thus, there is a need for an improved particle monitoring apparatus that allows an air sample to be drawn into a particle counter at a constant flow rate. Such an apparatus will more readily facilitate acquisition and evaluation of the air sample.

SUMMARY OF THE INVENTION

Exemplary embodiments of the present invention provide a flow indicator that indicates an air sample flow rate through the flow indicator. Exemplary embodiments of the present invention also provide a particle monitoring apparatus comprising such a flow indicator.

In one embodiment, the invention provides a flow indicator comprising a housing and a floater. The housing has at least one lower inlet port, wherein the housing is adapted to draw an air sample through the at least one lower inlet port, an interior space adapted to allow air to pass through the interior space, an upper outlet port, wherein the housing is adapted to exhaust the air sample through the upper outlet port, and a transparent window adapted to display a portion of the interior space. The floater is disposed inside the housing and is adapted to move substantially vertically in accordance with a flow of the air sample. The floater is also adapted to indicate a flow rate of the air sample.

In another embodiment, the invention provides a particle monitoring apparatus comprising a sampling probe disposed substantially horizontally and adapted to draw a first air sample, a flow indicator coupled to a lower portion of the sampling probe in a substantially vertical direction and adapted to draw a second air sample to indicate a flow rate of the second air sample, and a particle counter connected to the sampling probe and adapted to count particles contained in the first and second air samples. The flow indicator comprises a housing and a floater. The housing has at least one lower inlet port, wherein the housing is adapted to draw the second air sample through the at least one lower inlet port, an interior space adapted to allow air to pass through the interior space, an upper outlet port, wherein the housing is adapted to exhaust the second air sample into the sampling probe through the upper outlet port, and a transparent window adapted to display a portion of the interior space. The floater is disposed inside the housing and is adapted to move substantially vertically in accordance with a flow of the second air sample. The floater is also adapted to indicate the flow rate of the second air sample.

BRIEF DESCRIPTION OF THE DRAWINGS

Exemplary embodiments of the present invention will be described in detail hereinafter with reference to the accompanying drawings, in which like reference symbols refer to like or similar elements throughout. In the drawings.

DESCRIPTION OF EXEMPLARY EMBODIMENTS

Figure 1:
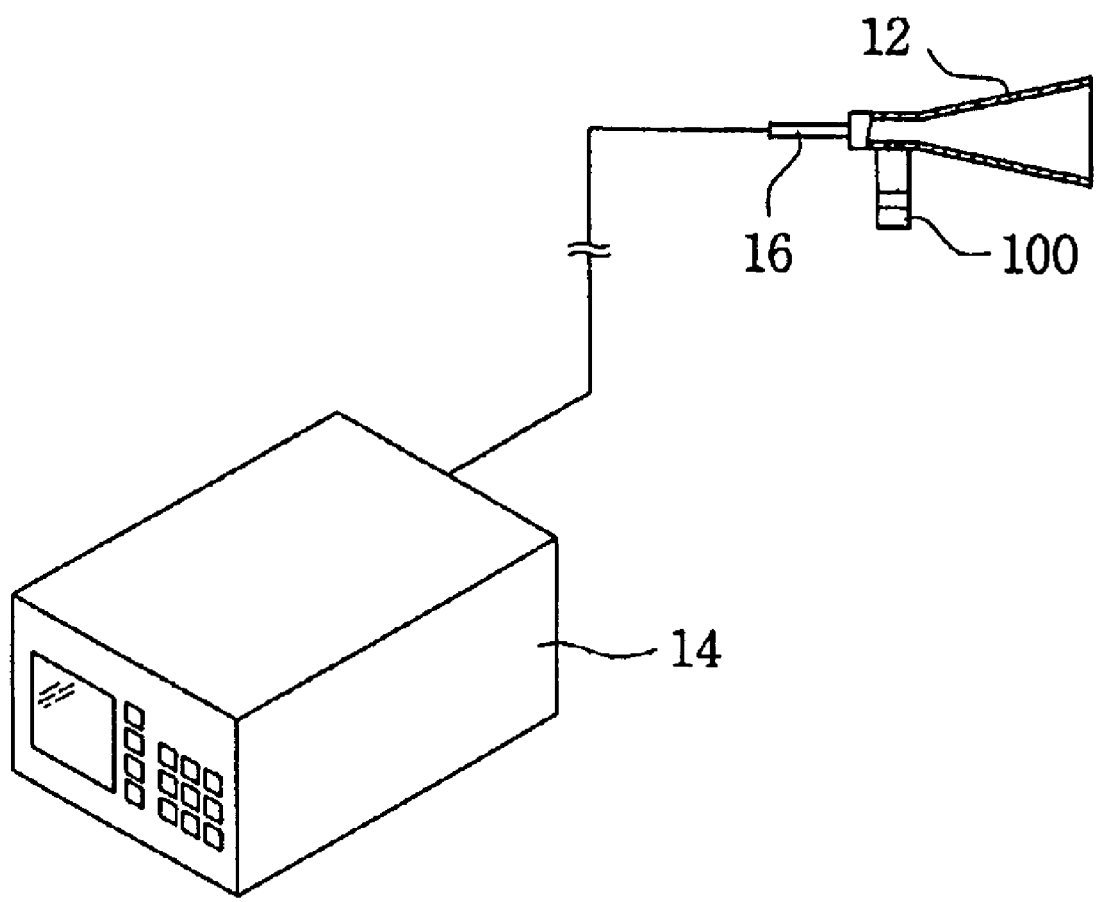
FIG. 1 is a schematic view illustrating a particle monitoring apparatus comprising a flow indicator in accordance with an exemplary embodiment of the present invention.

As used herein, the term "and/or" includes any and all combinations of one or more of the associated listed items.

It will be understood that, although the terms first, second, etc. may be used herein to describe various elements, these elements should not be limited by these terms. These terms are only used to distinguish one element from another. For example, a first thin film could be termed a second thin film, and, similarly, a second thin film could be termed a first thin film without departing from the teachings of the disclosure.

The terminology used herein is used only for the purpose of describing particular embodiments of the invention and is not intended to limit the invention.

Furthermore, relative terms, such as "lower" or "bottom" and "upper" or "top," may be used herein to describe one element's relationship to another element or other elements illustrated in the drawings. It will be understood that relative terms are intended to encompass different orientations of an element in addition to the orientation depicted in the drawings. For example, if a first element in one of the drawings is turned over, secondary elements described as being on the "lower" side the first element would then be oriented on "upper" side of the first element. Therefore, the exemplary term "lower" can encompasses both an orientation of "lower" and "upper," depending of the particular orientation of one or more elements in the drawing. Similarly, if a first element in one of the drawings is turned over, secondary elements described as "below" or "beneath" the first element would then be oriented "above" the first element. Therefore, the exemplary terms "below" or "beneath" can encompass both an orientation of above and below.

Embodiments of the present invention are described herein with reference to cross-sectional illustrations that are schematic illustrations of idealized embodiments of the present invention. As such, variations from the shapes shown in the illustrations as a result of, for example, manufacturing techniques and/or tolerances, are to be expected. Thus, embodiments of the present invention should not be construed as being limited to the particular shapes of regions illustrated herein, but are to include deviations in shapes that result from, for example, manufacturing. For example, a region illustrated or described as flat may, typically, have rough and/or nonlinear features. Moreover, sharp angles illustrated in the drawings may be rounded. Thus, the regions illustrated in the drawings are schematic in nature and their shapes are not intended to illustrate the precise shape of a region and are not intended to limit the scope of the present invention.

FIG. 1 is a schematic view illustrating a particle monitoring apparatus comprising a flow indicator in accordance with an exemplary embodiment of the present invention.

Referring to FIG. 1, a particle monitoring apparatus 10 may be used to monitor the inner environment of a clean room in which semiconductor devices are manufactured. Particularly, particle monitoring apparatus 10 may be used to measure the concentration of particles in a primary air sample taken from the interior of a clean room.

The primary air sample may comprise a first air sample drawn by a sampling probe 12 and a second air sample drawn by a flow indicator 100 coupled to sampling probe 12. In more detail, sampling probe 12 is disposed in a clean room and draws the first air sample. Flow indicator 100 is coupled vertically to sampling probe 12 and draws the second air sample. An "entire flow rate" associated with the first and second air samples may be determined on the basis of the ascertained flow rate for the second air sample.

A particle counter 14 may be connected to sampling probe 12 by a sampling tube 16. Although not shown in detail in the drawings, particle counter 14 may comprise a laser optical member adapted to detect the particles in the primary air sample and a pump adapted to provide the suction force necessary to draw in the primary air sample. Alternatively, particle monitoring apparatus 10 may comprise a condensation particle counter.

Figure 2:
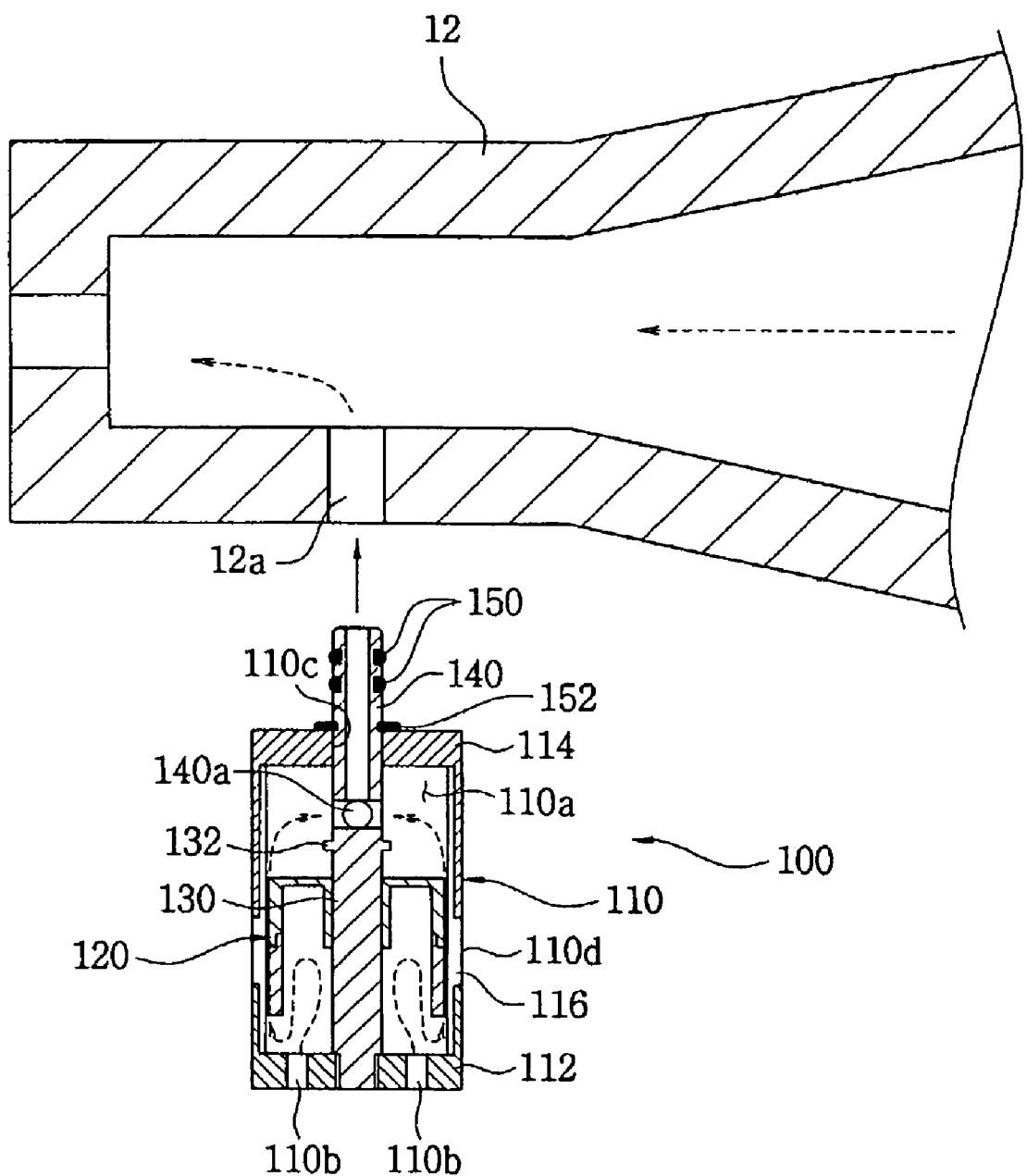
FIG. 2 is a cross-sectional view illustrating a sampling probe shown in FIG. 1 and the flow indicator shown in FIG. 1.

FIG. 2 is a cross-sectional view illustrating sampling probe 12 and flow indicator 100 shown in FIG. 1.

In the illustrated example, sampling probe 12 has a funnel shape and is usually intended to be mounted or disposed in a horizontal manner (e.g., relative to a wall of the clean room). Assigning a horizontal orientation to sampling probe 12, flow indicator 100 is coupled substantially vertically to a lower portion of sampling probe 12.

Flow indicator 100 may comprise a housing 110 that has an interior space 110a, which is used as a flow passage for the second air sample, and a floater 120 disposed in interior space 110a. Housing 110 has a cylindrical shape and is disposed in a vertical direction. Further, housing 110 has a plurality of lower inlet ports 110b, through which the second air sample is drawn into flow indicator 100, and an upper outlet port 110c, through which the second air sample that passes through interior space 110a is exhausted into sampling probe 12. Housing 110 also comprises a transparent window 110d, through which interior space 110a may be observed. Floater 120 may move in the vertical direction within housing 110 in accordance with the flow of the second air sample through interior space 110a.

Additionally, housing 110 may comprise a lower cap 112 having the plurality of lower inlet ports 110b, an upper cap 114 having upper outlet port 110c, and a transparent tube 116 coupled between lower and upper caps 112 and 114 and which serves as transparent window 110d. Transparent tube 116 is inserted into lower and upper caps 112 and 114 with an interference fit to prevent the second air sample from leaking out of housing 110 once it has been drawn into interior space 110a.

Guide member 130 is disposed inside of housing 110 and guides the movement of floater 120. Guide member 130 extends upwardly from a lower portion of housing 110. In more detail, guide member 130 extends upwardly from a lower central portion of housing 110 along a central axis of housing 110, and floater 120 has a central hole through which guide member 130 passes. In addition, a ring-shaped stopper 132 is disposed at an upper portion of guide member 130 to limit the height to which floater 120 may rise (i.e., to keep floater 120 from moving to a point above stopper 132).

The second air sample drawn through the plurality of lower inlet ports 110b flows from a lower portion of interior space 110a into an upper portion of interior space 110a through a gap between housing 110 and floater 120, and is then exhausted into sampling probe 12 through an exhaust pipe 140 extending through upper outlet port 110c.

Exhaust pipe 140 has a plurality of holes 140a through which the second air sample is drawn in order to exhaust the second air sample after the second air sample has flowed into the upper portion of interior space 110a. Holes 140a are formed radially around a lower portion of exhaust pipe 140. In the illustrated example shown in FIGS. 2 and 6, exhaust pipe 140 is disposed coaxially with guide member 130, and exhaust pipe 140 and guide member 130 are formed as one linear piece. However, guide member 130 and exhaust pipe 140 may be provided separately.

Sampling probe 12 has a coupling hole 12a formed through a lower portion of sampling probe 12, and exhaust pipe 140 is coupled inside of coupling hole 12a with an interference fit, thereby coupling flow indicator 100 with sampling probe 12. When flow indicator 100 and sampling probe 12 are coupled in this manner, sealing members 150 may be interposed between coupling hole 12a and exhaust pipe 140 to prevent leakage of the first and second air samples. For example, O-rings may be interposed between coupling hole 12a and exhaust pipe 140, and when O-rings are interposed between coupling hole 12a and exhaust pipe 140, flow indicator 100 is fixed to sampling probe 12 by the O-rings. Further, a fixing clip 152 may be disposed at exhaust pipe 140 to limit the position at which exhaust pipe 140 may be coupled to housing 110.

Figure 3:
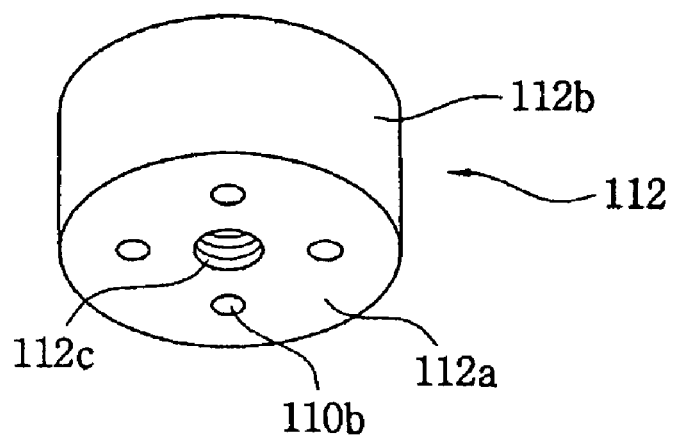
FIG. 3 is a perspective view illustrating a lower cap shown in FIG. 2.
Figure 4:
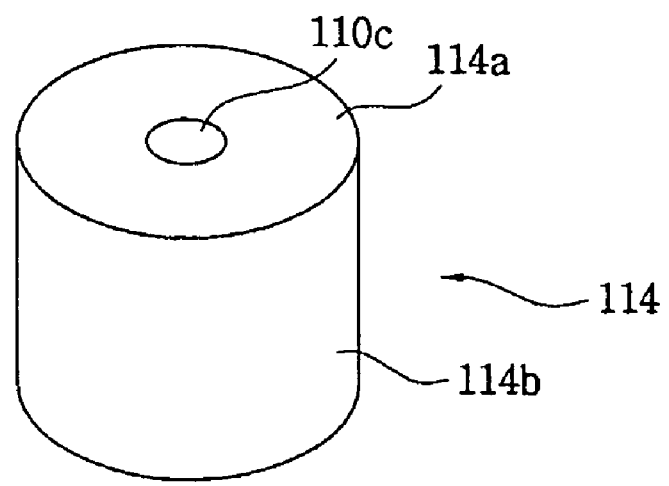
FIG. 4 is a perspective view illustrating an upper cap shown in FIG. 2.
Figure 5:
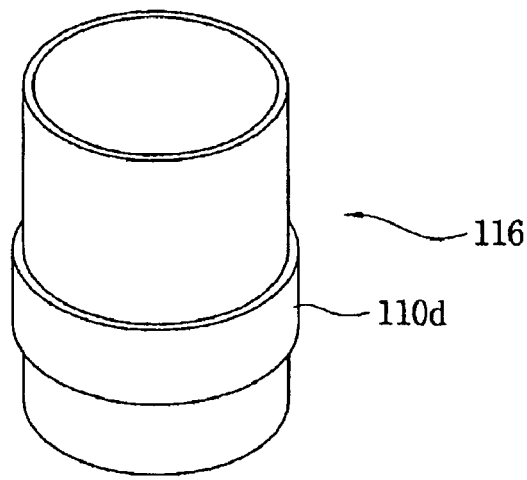
FIG. 5 is a perspective view illustrating a transparent tube shown in FIG. 2.
Figure 6:
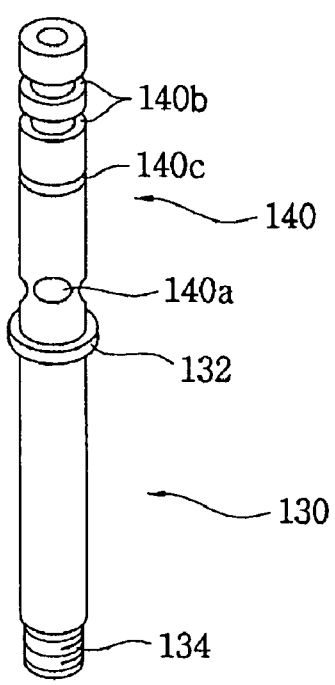
FIG. 6 is a perspective view illustrating a guide member and an exhaust pipe shown in FIG. 2.

FIGS. 3, 4, and 5 are perspective views illustrating lower cap 112, upper cap 114, and transparent tube 116, respectively, each of which is shown in FIG. 2. FIG. 6 is a perspective view illustrating guide member 130 and exhaust pipe 140 as shown in FIG. 2.

Referring to FIGS. 3 through 6, lower cap 112 has a cylindrical shape and has a closed lower end and an open upper end (i.e., the lower end is covered by a lower panel 112a, while the upper end is not covered). On the contrary, upper cap 114 has a cylindrical shape and has a closed upper end and an open lower end (i.e., the upper end of upper cap 114 is covered by an upper panel 114a, while the lower end is not covered).

Particularly, lower cap 112 comprises lower panel 112a, and a lower tube 112b extending upwardly from lower panel 112a and having a first length in a direction perpendicular to lower panel 112a. Also, lower panel 112a has the plurality of lower inlet ports 110b. Upper cap 114 comprises upper panel 114a, and an upper tube 114b extending downwardly from the upper panel 114a and having a second length in a direction perpendicular to upper panel 114a. Also, upper panel 114a has upper outlet port 110c.

Lower inlet ports 110b are arranged radially around the center of lower panel 112a. Lower inlet ports 110b may be arranged at regular intervals along a circle concentric to the circumference of lower panel 112a as desired. Though four lower inlet ports 110b are arranged radially around the center of lower panel 112a shown in FIG. 3, the scope of the present invention is not limited by the number of lower inlet ports 110b shown in FIG. 3.

A threaded hole 112c is formed through a central portion of lower cap 112. Threaded hole 112c is used to couple lower cap 112 to guide member 130, and guide member 130 has a threaded end portion 134 that is threadably engaged with threaded hole 112c. As shown in the drawings, guide member 130 has a circular horizontal cross-section. However, guide member 130 may have a polygonal horizontal cross-section to prevent floater 120 from rotating.

Transparent tube 116 is provided so that the movement of floater 120 in interior space 110a, which is caused by the flow of the second air sample, may be observed visually. Transparent tube 116 has a third length along a central axis of transparent tube 116 that is longer than the sum of the first length of lower tube 112b and the second length of upper tube 114b so that floater 120 in interior space 110a may be observed. Transparent tube 116 also has an inner diameter that is constant along the third length so that floater 120 will move stably within transparent tube 116. Furthermore, transparent tube 116 may comprise outer step portions (i.e., the upper and lower portions of transparent window 110d of FIG. 5) that bound the respective positions at which each of lower and upper caps 112 and 114 may be coupled to transparent tube 116, as shown in FIGS. 2 and 5.

Exhaust pipe 140 and guide member 130 are provided in one piece. A plurality of first annular grooves 140b is formed in an upper portion of exhaust pipe 140, and a sealing member 150 (of FIG. 2) is mounted in each of the plurality of first annular grooves 140b. A second annular groove 140c is formed adjacent to the plurality of first annular grooves 140b, and fixing clip 152, which limits the position at which guide member 130 and exhaust pipe 140 may be coupled to housing 110, is mounted in second annular groove 140c.

Figure 7:
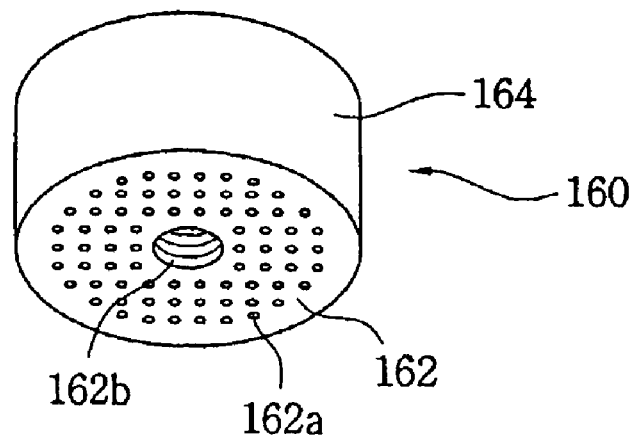
FIG. 7 is a perspective view illustrating another exemplary embodiment of the lower cap shown in FIG. 3.
Figure 8:
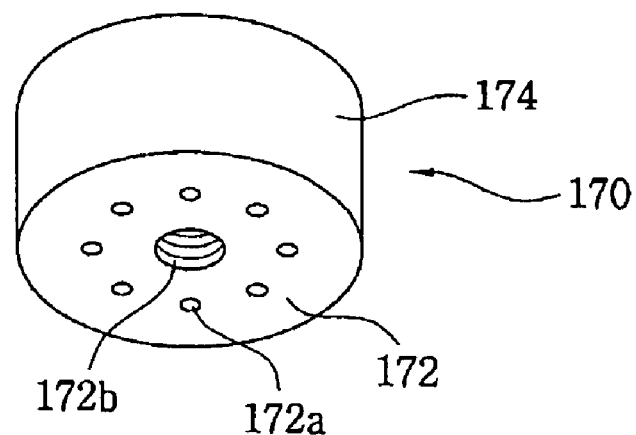
FIG. 8 is a perspective view illustrating yet another exemplary embodiment of the lower cap as shown in FIG. 3.

FIGS. 7 and 8 are perspective views illustrating other exemplary embodiments of lower cap 112 of FIGS. 2 and 3.

Referring to FIG. 7, a lower cap 160 may comprise a lower panel 162, which has a plurality of fine inlet ports 162a uniformly formed in lower panel 162 and used to draw the second air sample into inner space 110a, and a lower tube 164 that extends upwardly from lower panel 162. In addition, lower panel 162 has a threaded hole 162b in a central portion of lower panel 162 by which lower cap 160 is coupled to guide member 130.

Referring to FIG. 8, a lower cap 170 may comprise a lower panel 172 having eight lower inlet ports 172a formed in lower panel 172, arranged at regular intervals along a circle concentric to the circumference of lower panel 172, and used to draw the second air sample into interior space 110a; and lower cap 170 may further comprise a lower tube 174 that extends upwardly from lower panel 172. Further, lower panel 172 has a threaded hole 172b in a central portion of lower panel 172 by which lower cap 170 is coupled to guide member 130. Each lower inlet port 172a has a diameter smaller than the diameter of each lower inlet port 110b of FIG. 3.

Referring to FIGS. 3, 7, and 8, the number of inlet ports 110b, 162a, and 172a formed in lower cap 112, 160, and 170, respectively, may vary. However, an entire cross-sectional area of inlet ports 110b, 162a, or 172a may be determined in accordance with the normal entire flow rate of the primary air sample, and the number and diameter of the inlet ports 110b, 162a, or 172a may be adjusted in accordance with the normal range of the entire flow rate of the primary air sample. For example, when the normal entire flow rate of the primary air sample ranges from about 4 to about 9 l/min, each of the lower inlet ports 110b (of FIG. 3) may have a diameter of about 4 mm.

Figure 9:
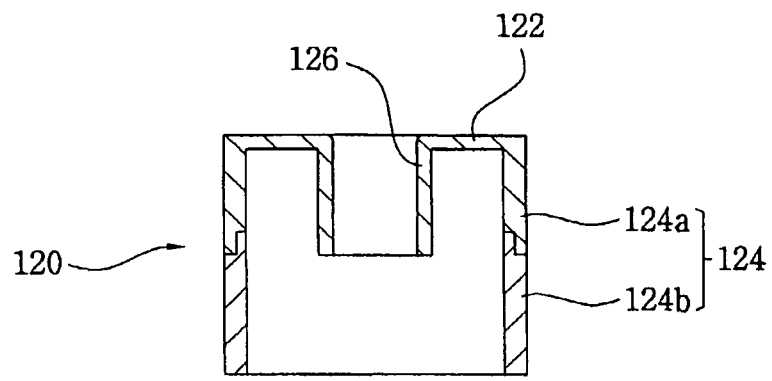
FIG. 9 is a cross-sectional view illustrating a floater shown in FIG. 2.

FIG. 9 is a cross-sectional view illustrating floater 120 of FIG. 2.

Referring to FIG. 9, floater 120 may comprise an inner panel 122, an outer tube 124, and a guide tube 126. Inner panel 122 has a disk shape, and guide member 130 passes through a central hole formed in a central portion of inner panel 122. Outer tube 124 extends downwardly from an outer edge portion of inner panel 122 and the outer surface of outer tube 124 faces an inner surface of transparent tube 116. Guide tube 126 extends downwardly from an inner portion of inner panel 122 and surrounds guide member 130 so that guide member 130 may guide the movement of floater 120 caused by the flow of the second air sample.

A first gap between guide tube 126 and guide member 130 is less than or equal to about 0.1 mm so that the second air sample can be restrained from flowing through the first gap. For example, the first gap between guide tube 126 and guide member 130 may be about 0.05 mm. A second gap between outer tube 124 and transparent tube 116 may be determined in accordance with the normal entire flow rate of the primary air sample. For example, when the normal entire flow rate of the primary air sample is about 4 to about 9 l/min, and an outer diameter of outer tube 124 is about 25 to about 26 mm, the second gap may be about 0.3 to about 0.5 mm.

Outer tube 124 may comprise a plurality of tubes, wherein each tube of the plurality of tubes is a different color in order to facilitate visual observation of the movement of floater 120 through transparent tube 116. Particularly, outer tube 124 comprises a first color tube 124a that extends downwardly from the outer edge portion of inner panel 122 and has a first color, and a second color tube 124b that is coupled to a lower end of first color tube 124a and has a second color different from the first color. For example, the first color and the second color may be red and blue, respectively. Step portions are formed at the lower portion of first color tube 124a and an upper portion of the second color tube 124b in order to provide an interference fit between first and second color tubes 124a and 124b.

The flow of the second air sample moves floater 120 vertically within interior space 110a, and the flow rate of the second air sample is ascertained by observing the position of floater 120 through transparent tube 116. For example, when the primary air sample is drawn at a normal flow rate, the second color of floater 120 (e.g., blue) will be visible through transparent tube 116. On the contrary, when the first color of floater 120 (e.g., red) is visible through transparent tube 116, the primary air sample is not being drawn at a normal flow rate. That is, when the flow rate of the second air sample is reduced below a normal flow rate, the first color of floater 120 is visible through transparent tube 116 because floater 120 has, as a result of the reduced flow rate of the second air sample, a lower position within interior space 110a than it has when the second air sample is being drawn at a normal flow rate for the second air sample. Particularly, when the second color of floater 120 is observed through transparent tube 116, the primary air sample has an entire flow rate of about 4 to about 9 l/min and is being drawn normally. When the first color of floater 120 is observed through transparent tube 116, the primary air sample has an entire flow rate of less than or equal to about 1 l/min and is being drawn abnormally. Further, when the first and second colors of floater 120 are observed through transparent tube 116 at the same time, the primary air sample is being drawn at an entire flow rate of about 2 to about 3 l/min.

The position of floater 120 can be easily observed with the naked eye by observing the color(s) of floater 120 visible through transparent tube 116. So, even when sampling probe 12 and flow indicator 100 are disposed adjacent to a ceiling of the clean room, an operator can easily ascertain whether or not the primary air sample is being drawn normally.

Figure 10:
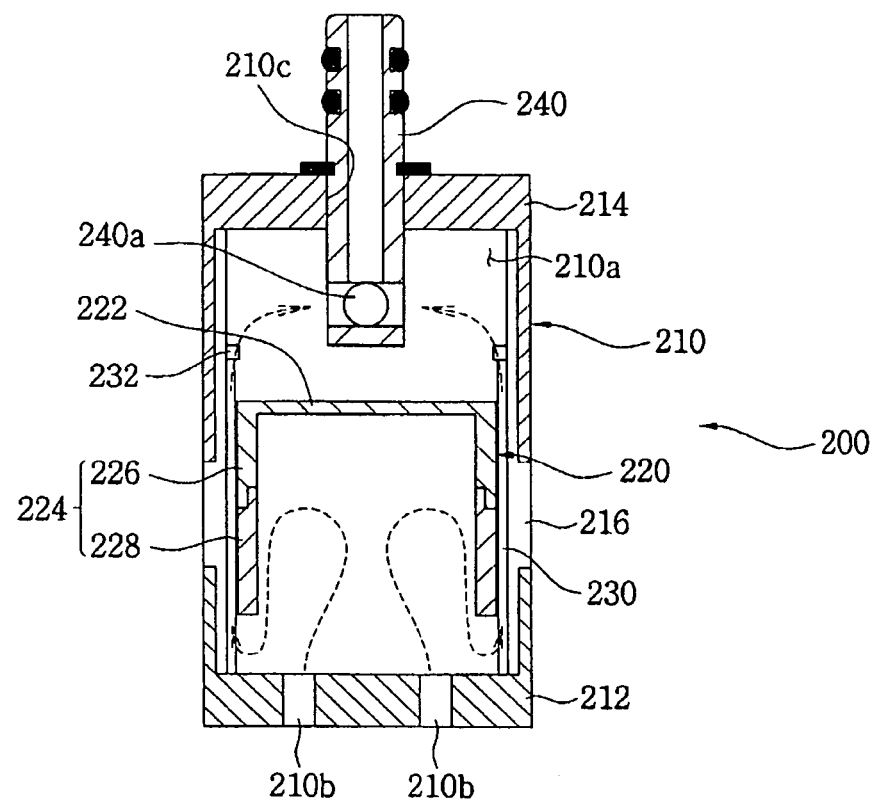
FIG. 10 is a vertical cross-sectional view illustrating a flow indicator in accordance with another exemplary embodiment of the present invention.
Figure 11:
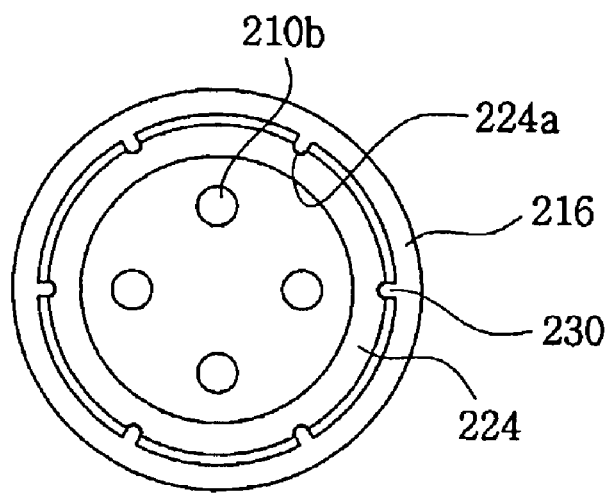
FIG. 11 is a horizontal cross-sectional view illustrating the flow indicator shown in FIG. 10.
Figure 12:
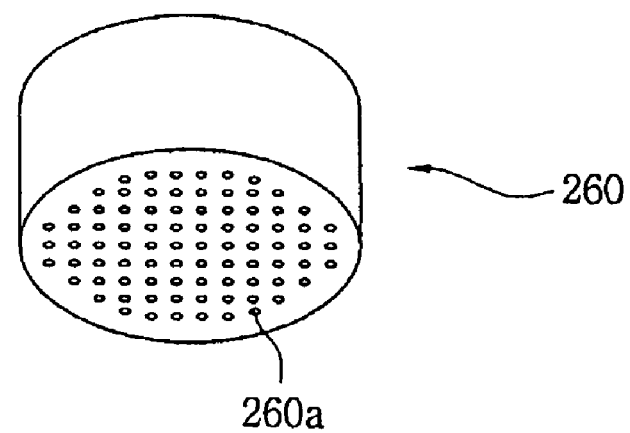
FIG. 12 is a perspective view illustrating another exemplary embodiment of a lower cap shown in FIG. 10.
Figure 13:
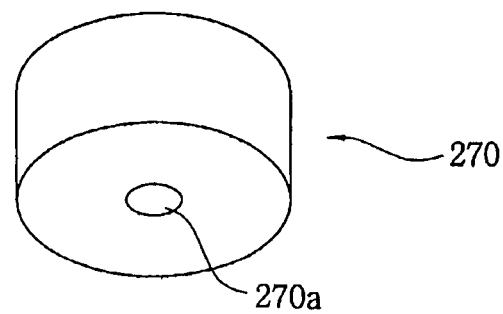
FIG. 13 is a perspective view illustrating yet another exemplary embodiment of the lower cap shown in FIG. 10.

FIG. 10 is a vertical cross-sectional view illustrating a flow indicator in accordance with another exemplary embodiment of the present invention, and FIG. 11 is a horizontal cross-sectional view illustrating the flow indicator shown in FIG. 10. FIGS. 12 and 13 are perspective views illustrating exemplary embodiments of the lower cap shown in FIG. 10.

Referring to FIGS. 10 and 11, a flow indicator 200, in accordance with an exemplary embodiment of the present invention, may comprise a cylindrical housing 210 comprising an interior space 210a and a floater 220 disposed within housing 210 and which may move vertically within housing 210.

Flow indicator 200 is coupled to a lower portion of a sampling probe that draws a first air sample. In addition, flow indicator 200 comprises a lower cap 212 having a plurality of lower inlet ports 210b through which a second air sample is drawn, an upper cap 214 having an upper outlet port 210c through which an exhaust pipe 240 is inserted, wherein exhaust pipe 240 is adapted to exhaust the second air sample, and a transparent tube 216 coupled between lower and upper caps 212 and 214.

Though lower cap 212 of FIG. 11 has four lower inlet ports 210b through which the second air sample may be drawn, the scope of the present invention is not limited by the number of lower inlet ports 210b shown in FIG. 11. For example, a lower cap 260 (shown in FIG. 12) may have a plurality of fine lower inlet ports 260a formed uniformly in lower cap 260, and a lower cap 270 (shown in FIG. 13) may have one lower inlet port 270a. Lower caps 260 and 270 are each alternate exemplary embodiments of lower cap 212 of flow indicator 200 of FIGS. 10 and 11.

Referring again to FIGS. 10 and 11, transparent tube 216 comprises a plurality of rails 230 that protrude from an inner surface of transparent tube 216 and extending substantially vertically to guide the movement of floater 220.

Floater 220 comprises an inner panel 222 that has the shape of a disk and is disposed in a direction substantially perpendicular to a central axis of housing 210, and an outer tube 224 that extends downwardly from an outer edge portion of inner panel 222. Outer tube 224 is separated from the inner surface of transparent tube 216, and a plurality of guide grooves 224a is formed in the outer surface of outer tube 224. The plurality of guide grooves 224a is adapted to engage with the plurality of rails 230. As an example, when (1) the entire flow rate of the first and second air samples is about 4 to about 9 l/min, (2) each of the four lower inlet ports 210b has an inner diameter of about 4 mm, and (3) the outer diameter of outer tube 224 is about 25 to about 26 mm, then the gap between outer tube 224 and transparent tube 216 may be about 0.3 to about 0.5 mm. Further, the gap between each rail 230 and its corresponding guide groove 224a may be less than or equal to about 0.1 mm.

Outer tube 224 comprises a first color tube 226 that extends downwardly from the outer edge portion of inner panel 222 and has a first color, and a second color tube 228 that is coupled to a lower end of first color tube 226 and has a second color different from the first color.

Each stopper 232 of a plurality of stoppers 232 is disposed on a rail 230 of the plurality of rails 230 to limit the height to which floater 220 may rise.

Exhaust pipe 240 extends through upper outlet port 210c of upper cap 214, and a lower end of exhaust pipe 240 is disposed higher than each of the plurality of stoppers 232. As shown in FIG. 10, exhaust pipe 240 comprises an open upper end, a closed lower end, and a plurality of holes 240a that are formed radially around a lower portion of exhaust pipe 240 and through which the second air sample is drawn out of housing 210. However, exhaust pipe 240 may have an open lower end.

Many of the elements of flow indicator 200 are similar or identical to those already described regarding flow indicator 100 shown in FIGS. 1 through 9, so further detailed description of those elements will be omitted herein.

Figure 14:
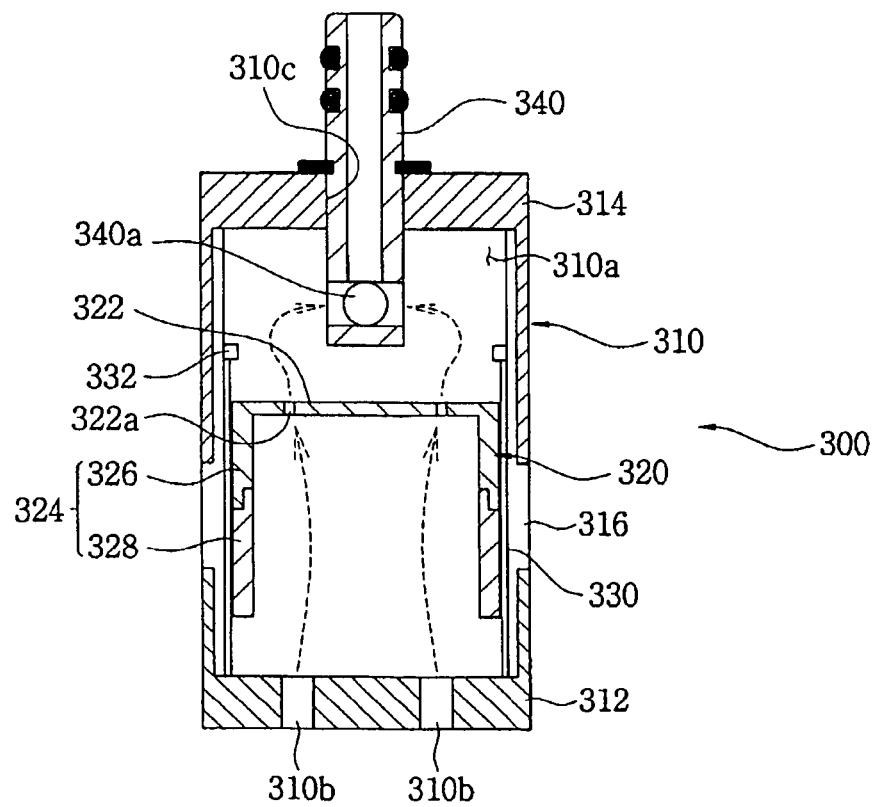
FIG. 14 is a vertical cross-sectional view illustrating a flow indicator in accordance with yet another exemplary embodiment of the present invention.
Figure 15:
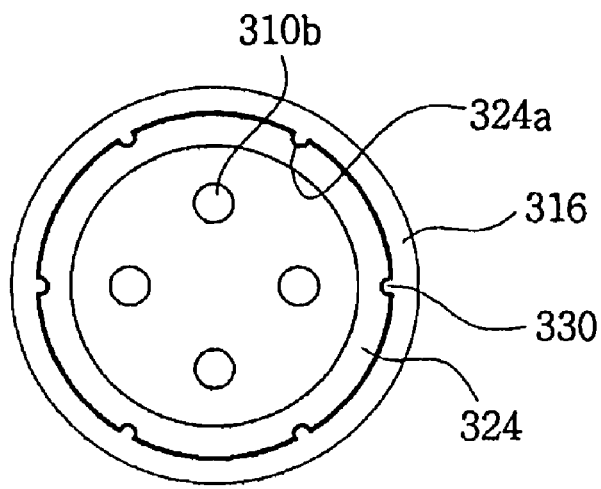
FIG. 15 is a horizontal cross-sectional view illustrating the flow indicator shown in FIG. 14.
Figure 16:
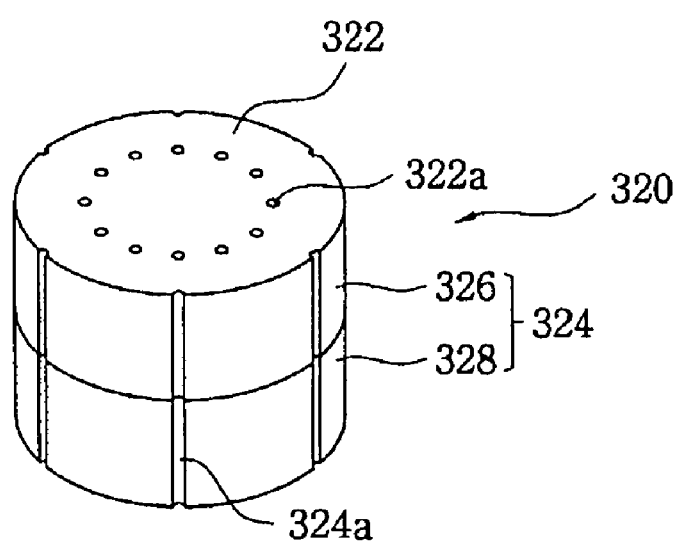
FIG. 16 is a perspective view illustrating a floater shown in FIG. 14.

FIG. 14 is a vertical cross-sectional view illustrating a flow indicator in accordance with yet another exemplary embodiment of the present invention, FIG. 15 is a horizontal cross-sectional view illustrating the flow indicator shown in FIG. 14, and FIG. 16 is a perspective view illustrating a floater shown in FIG. 14.

Referring to FIGS. 14 through 16, a flow indicator 300, in accordance with an exemplary embodiment of the present invention, may comprise a cylindrical housing 310 comprising an interior space 310a and a floater 320 disposed within housing 310 and which may move vertically within housing 310.

Flow indicator 300 is coupled substantially vertically to a lower portion of a sampling probe adapted to draw a first air sample. Housing 310 may comprise a lower cap 312 having a plurality of lower inlet ports 310b through which a second air sample may be drawn. Housing 310 may also comprise an upper cap 314 having an upper outlet port 310c through which an exhaust pipe 340, which is adapted to exhaust the second air sample into the sampling probe, is disposed, and a transparent tube 316 coupled between lower and upper caps 312 and 314.

Transparent tube 316 comprises a plurality of rails 330, which protrude from an inner surface of transparent tube 316, extend substantially vertically, and which are adapted to guide the vertical movement of floater 320.

Floater 320 may comprise an inner panel 322 disposed in a direction substantially perpendicular to a central axis of housing 310. Inner panel 322 may have a plurality of first holes 322a through which the second air sample may pass. Floater 320 may further comprise an outer tube 324 that extends downwardly from an outer edge portion of inner panel 322 and comprises a plurality of guide grooves 324a adapted to engage with the plurality of rails 330. A first gap between outer tube 324 and transparent tube 316 may be less than or equal to about 0.1 mm. Also, one of a plurality of second gaps is formed between each rail 330 and its corresponding guide groove 324a. Each of the plurality of second gaps may be less than or equal to about 0.1 mm.

Outer tube 324 comprises a first color tube 326 that extends downwardly from the outer edge portion of inner panel 322 and has a first color, and a second color tube 328 that is coupled to a lower end of first color tube 326 and has a second color different from the first color.

Flow indicator 300 also comprises a plurality of stoppers 332. Each of the plurality of stoppers 332 is disposed on a rail 330 of the plurality of rails 330 to limit the height to which floater 320 may rise.

Exhaust pipe 340 extends through upper outlet port 310c of upper cap 314, and a lower end of exhaust pipe 340 is disposed higher than each of the plurality of stoppers 332. As shown in FIG. 14, exhaust pipe 340 comprises an open upper end, a closed lower end, and a plurality of second holes 340a that are formed radially around a lower portion of exhaust pipe 340 and through which the second air sample may be drawn out of housing 310. However, exhaust pipe 340 may have an open lower end.

Many of the elements of flow indicator 300 are similar or identical to those already described regarding flow indicator 100 shown in FIGS. 1 through 9 or flow indicator 200 shown in FIGS. 10 through 13, so further detailed description of those elements will be omitted herein.

Figure 17:
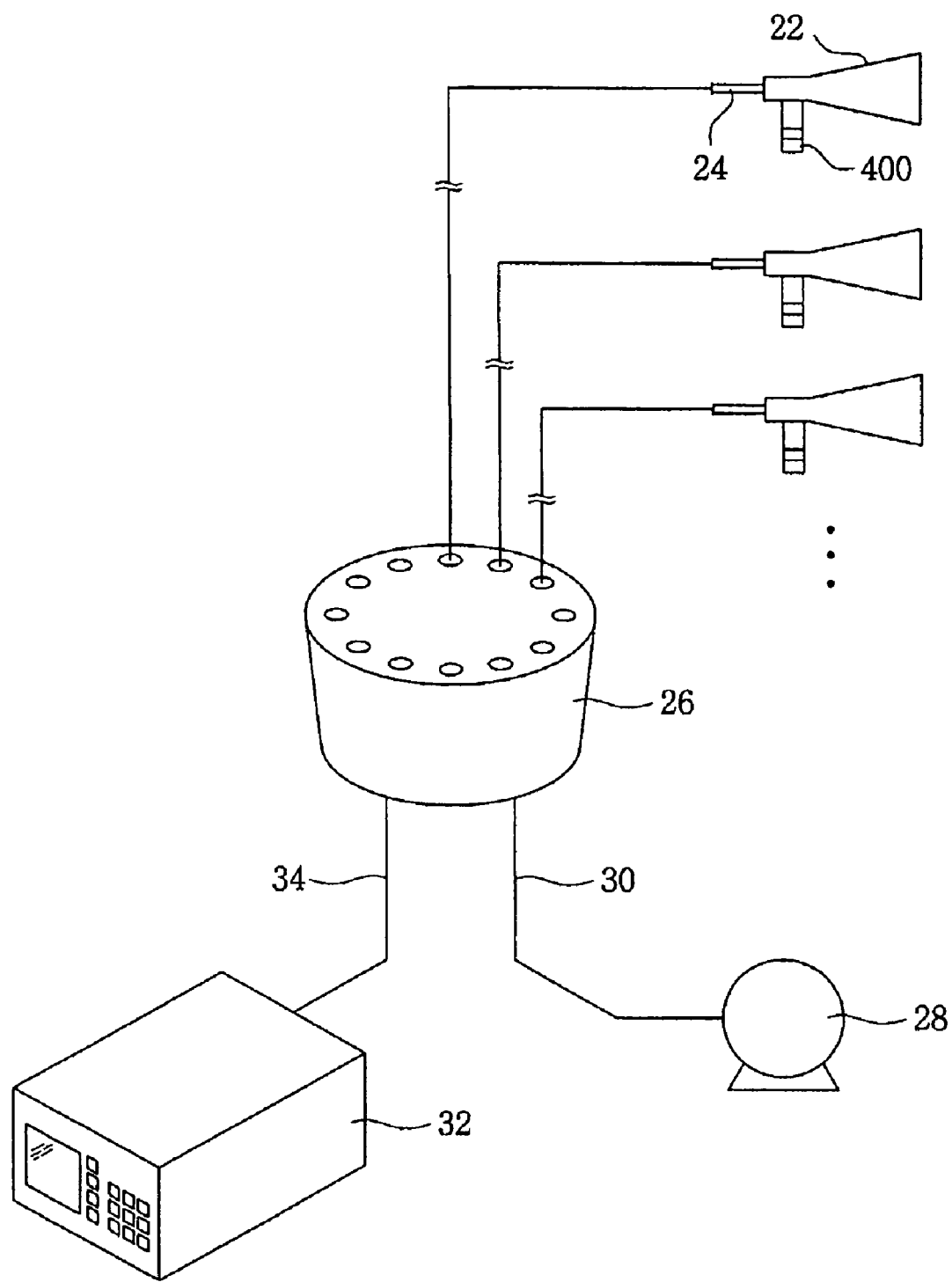
FIG. 17 is a schematic view illustrating a particle monitoring apparatus in accordance with still another exemplary embodiment of the present invention.

FIG. 17 is a schematic view illustrating a particle monitoring apparatus in accordance with still another exemplary embodiment of the present invention.

Referring to FIG. 17, a particle monitoring apparatus 20, in accordance with an exemplary embodiment of the present invention, may comprise a plurality of sampling probes 22 located in several places in a clean room and a plurality of flow indicators 400, each of which is coupled to a sampling probe 22 of the plurality of sampling probes 22. Each sampling probe 22 is adapted to draw a primary air sample and each flow indicator 400 is adapted to indicate the flow rate of the primary air sample.

Each sampling probe 22 is connected to a manifold 26 by one of a plurality of sampling tubes 24. Manifold 26 is connected by a suction tube 30 to a first pump 28 adapted to draw the primary air samples. In addition, manifold 26 is connected by a second sampling tube 34 to a particle counter 32 adapted to count particles in the primary air samples. In particular, manifold 26 is adapted to selectively provide the primary air samples drawn from the locations of sampling probes 22 to particle counter 32. Particle counter 32 may comprise a laser optical member adapted for use in counting particles contained in the selected primary air sample, and may also comprise a second pump adapted to draw the selected air sample into particle counter 32.

Further detailed descriptions of sampling probes 22 and flow indicators 400 will be omitted because each of sampling probes 22 and flow indicators 400 is similar or identical to sampling probes and flow indicators, respectively, that have already been described in connection with previously described exemplary embodiments of the present invention.

In accordance with exemplary embodiments of the present invention, an air sample is provided to the particle counter to measure the degree of contamination of the clean room. The flow rate of the air sample may be easily ascertained by observing the floater through the transparent tube; and thus, the reliability of a measurement of the degree of contamination of the clean room taken by the particle counter may be improved.

Further, the flow rate of the air sample may be observed visually at any time. Thus, there is no need to separately check the operation of the particle monitoring apparatus, and the time required check the operation (or operating state) of the particle monitoring apparatus may be reduced. Consequently, the cleanliness of the clean room may be maintained constantly. Furthermore, deterioration in the cleanliness of the clean room caused by variation in the flow rate of the air samples may be prevented.

Although exemplary embodiments of the present invention have been described herein, the present invention is not limited to the exemplary embodiments described. Rather, those skilled in the art will recognize that various changes and modifications can be made to the exemplary embodiments while remaining within the scope of the present invention as defined by the following claims.

What is claimed is:

1. A particle monitoring apparatus comprising:
   a sampling probe disposed substantially horizontally and adapted to draw a first air sample, wherein the sampling probe is disposed in a clean room adapted for use in the manufacture of a semiconductor device;
   a flow indicator coupled to a lower portion of the sampling probe in a substantially vertical direction and adapted to draw a second air sample to indicate a flow rate for the second air sample; and,
   a particle counter connected to the sampling probe and adapted to count particles contained in the first and second air samples,
   wherein the flow indicator comprises:
      a housing arranged substantially in a vertical manner and having:
         a lower inlet port adapted to draw an air sample;
         an interior space adapted to pass the air sample;
         an upper outlet port adapted to exhaust the air sample; and,
         a transparent window adapted to allow visual observation of
      at least a portion of the interior space; and,
      a floater disposed within the housing and adapted to move substantially vertically in response to the flow of the air sample to indicate a flow rate for the air sample.

2. A particle monitoring apparatus comprising:
   a sampling probe disposed substantially horizontally and adapted to draw a first air sample;
   a flow indicator coupled to a lower portion of the sampling probe in a substantially vertical direction and adapted to draw a second air sample to indicate a flow rate for the second air sample; and,
   a particle counter connected to the sampling probe and adapted to count particles contained in the first and second air samples,
   wherein the flow indicator comprises:
      a housing arranged substantially in a vertical manner and having:
         a lower inlet port adapted to draw an air sample;
         an interior space adapted to pass the air sample;
         an upper outlet port adapted to exhaust the air sample; and,
         a transparent window adapted to allow visual observation of
      at least a portion of the interior space;
      a floater disposed within the housing and adapted to move substantially vertically in response to the flow of the air sample to indicate a flow rate for the air sample; and,
      an exhaust pipe extending through the upper outlet port and adapted to exhaust the second air sample into the sampling probe.

3. The apparatus of claim 2, wherein the lower portion of the sampling probe has a coupling hole, and wherein the exhaust pipe is coupled to the coupling hole with an interference fit.

4. The apparatus of claim 3, wherein a sealing member is interposed between the coupling hole and the exhaust pipe, wherein the sealing member is adapted to prevent leakage of the first and second air samples.

* * * * *